(12) United States Patent
Silvis et al.

(10) Patent No.: US 6,823,268 B2
(45) Date of Patent: Nov. 23, 2004

(54) ENGINE EXHAUST EMISSIONS MEASUREMENT CORRECTION

(75) Inventors: William Martin Silvis, Ann Arbor, MI (US); Norbert Kreft, Ann Arbor, MI (US); Geraki Marek, Ann Arbor, MI (US); Wolfgang Schindler, Graz (AT)

(73) Assignee: AVL North America Inc., Plymouth, MI (US)

( * ) Notice: Subject to any disclaimer, the term of this patent is extended or adjusted under 35 U.S.C. 154(b) by 306 days.

(21) Appl. No.: 10/067,102

(22) Filed: Feb. 4, 2002

(65) Prior Publication Data

US 2003/0149536 A1 Aug. 7, 2003

(51) Int. Cl.$^7$ .......................... G06F 19/00; G01N 37/00
(52) U.S. Cl. ................ 702/30; 73/23.21; 73/23.31; 73/23.41; 73/29.01
(58) Field of Search .............. 702/30, 31, 24, 702/100; 73/23.21, 23.31, 23.41, 29.01; 60/274; 436/179

(56) References Cited

U.S. PATENT DOCUMENTS

| | | | |
|---|---|---|---|
| 5,846,831 A | | 12/1998 | Silvis |
| 5,968,452 A | | 10/1999 | Silvis |
| 6,085,582 A | * | 7/2000 | Tripathi et al. ............. 73/118.1 |
| 6,134,942 A | * | 10/2000 | Pasquereau et al. ........ 73/23.31 |
| 6,200,819 B1 | * | 3/2001 | Harvey et al. ............... 436/179 |
| 6,382,014 B1 | * | 5/2002 | Breton ....................... 73/23.31 |
| 6,387,706 B1 | * | 5/2002 | Eden ........................... 436/127 |
| 6,516,656 B1 | * | 2/2003 | Jetter et al. ................. 73/118.1 |
| 6,615,677 B2 | * | 9/2003 | Dickson et al. ........... 73/863.01 |
| 6,623,975 B1 | * | 9/2003 | Tefft et al. ................... 436/137 |
| 2001/0029775 A1 | * | 10/2001 | Uchihara et al. ........... 73/28.01 |
| 2002/0059033 A1 | * | 5/2002 | Batug et al. .................. 702/24 |
| 2002/0166390 A1 | * | 11/2002 | Graze, Jr. ................. 73/863.61 |
| 2003/0136177 A1 | * | 7/2003 | Hendren et al. ........... 73/23.31 |
| 2003/0167859 A1 | * | 9/2003 | Dickson et al. ........... 73/863.02 |

* cited by examiner

Primary Examiner—Patrick Assouad
(74) Attorney, Agent, or Firm—Carlson, Gaskey & Olds PC

(57) ABSTRACT

An exhaust emission analysis system is provided that includes an exhaust and dilution gas source respectively providing exhaust and dilution gases. A dilution unit includes exhaust and dilution gas flow devices, such as mass flow controllers, fluidly connected to the exhaust and dilution gas sources, respectively. The metering device in the mass flow controllers defines a gas flow rate of gas from its respective gas source. The gas flow devices are fluidly connected at a connection that mixes the gases to provide a diluted exhaust gas having an incorrect dilution ratio. A water measurement device such as an analyzer measures the water content of the exhaust gas, preferably subsequent to dilution. A water content dilution signal corresponding to the water content in the exhaust gas is sent from the water measurement device to a control device. An adjustment factor is calculated by the controller and a flow rate command signal is sent from the controller corresponding to the adjustment factor, preferably, to the exhaust gas mass flow controller to adjust the gas flow rate of the exhaust gas and provide a corrected dilution ratio at the connection. Correction of the diluted exhaust gas ratio may also be provided to particulate samplers according to the above principles.

72 Claims, 2 Drawing Sheets

ENGINE EXHAUST EMISSIONS MEASUREMENT CORRECTION

BACKGROUND OF THE INVENTION

This invention relates to engine exhaust emissions measurement methods and equipment, and more particularly, the invention relates to a method and apparatus for correcting sample exhaust gas flow through a mini-diluter.

Accuracy in taking engine exhaust emission measurements has become increasingly important in recent years in view of more stringent vehicle emission standards. Permissible emissions under these standards are very low such that the accuracy currently acceptable emission equipment may not be sufficient to distinguish between a vehicle with acceptable emission levels and a vehicle with unacceptable emission levels.

One system that is frequently used to test emissions is referred to as a mini-diluter in which the exhaust emissions are diluted to a lower sample concentration and then a portion of the sample is either analyzed online or stored in a bag for analysis. The dilution unit must be calibrated so that the exhaust emissions are diluted to obtain a dilution ratio that must remain constant throughout the test. In particular, the flow of a dilution gas (diluent), such as nitrogen or synthetic air, and the exhaust gas is set to obtain a desired dilution ratio in order to avoid water condensation in the sampling system. Typically thermal mass flow controllers are used to control the flow of the diluent and raw exhaust gas. Due to their measurement principle thermal mass flow controllers or meters show a strong dependency of the reading on the chemical composition of the measured gas. However, the exhaust gas has a different density and specific heat than the diluent such that when exhaust gas flows through the metering device in the dilution unit an incorrect dilution ratio is obtained. As a result, the sample collected in the bag does not accurately represent the exhaust gas emissions expelled from the vehicle and an inaccurate result is obtained.

The prior art has masked this inaccuracy by adjusting the amount of sample collected in the bag rather than adjusting the flow rate of exhaust gas emissions to obtain the correct dilution ratio. Data collected on the exhaust gas flow rate is therefore inaccurate. Increased accuracy may be necessary for post-analysis. Another common method is to calibrate the exhaust gas mass flow controller with a mixture of $CO_2$ and Nitrogen; this method does not account for changes of the exhaust gas composition and for the effects of the water content.

Partial flow particulate samplers, which measure the particulates in diesel emissions, also utilize mass flow controllers that are calibrated in a similar manner to that of mini-diluters. As a result, partial flow particulate samplers may also have inaccuracies. Therefore, what is needed is an engine exhaust emission measurement correction that yields a correct dilution ratio.

SUMMARY OF THE INVENTION AND ADVANTAGES

The present invention provides an exhaust emission analysis system including a dilution gas source respectively providing dilution gas. A dilution unit includes exhaust and dilution gas flow devices, such as mass flow controllers, fluidly connected to the exhaust and dilution gas sources, respectively. The metering devices in the mass flow controllers define a gas flow rate of gas from its respective gas source. The gas flow devices are fluidly connected at a connection that mixes the gases to provide a diluted exhaust gas having an incorrect dilution ratio if no further adjustment was performed. A humidity measurement device such as an analyzer measures the water content of the exhaust gas, preferably subsequent to dilution. A humidity content signal corresponding to the water content in the exhaust gas is sent from the water measurement device to a control device. The $CO_2$ content of the exhaust gas may be calculated using the chemical analysis of the fuel and the air/fuel ratio or by directly measuring the $CO_2$ content. An adjustment factor is calculated by the controller and a flow rate command signal is sent from the controller corresponding to the adjustment factor, preferably, to the exhaust gas mass flow controller to adjust the gas flow rate of the exhaust gas and provide a corrected dilution ratio at the connection.

The present invention also provides a system having a particulate sampler that includes a probe for proving exhaust gas. The particulate sampler has a mixer introducing the dilution gas to the exhaust gas to produce diluted exhaust gas, which has an uncorrected dilution ratio. Diluted exhaust and dilution gas flow devices are fluidly connected to the diluted exhaust and dilution gas sources respectively. The flow devices define a gas flow rate of gas from its respective gas source. Similar to the exhaust emission analysis system described above, a water content and/or carbon dioxide content may be determined which may be used in calculating an adjustment factor to provide a corrected dilution ratio at the mixer.

Accordingly, the above invention provides an engine exhaust emission measurement correction that yields a correct dilution ratio.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENT

Figure 1A:
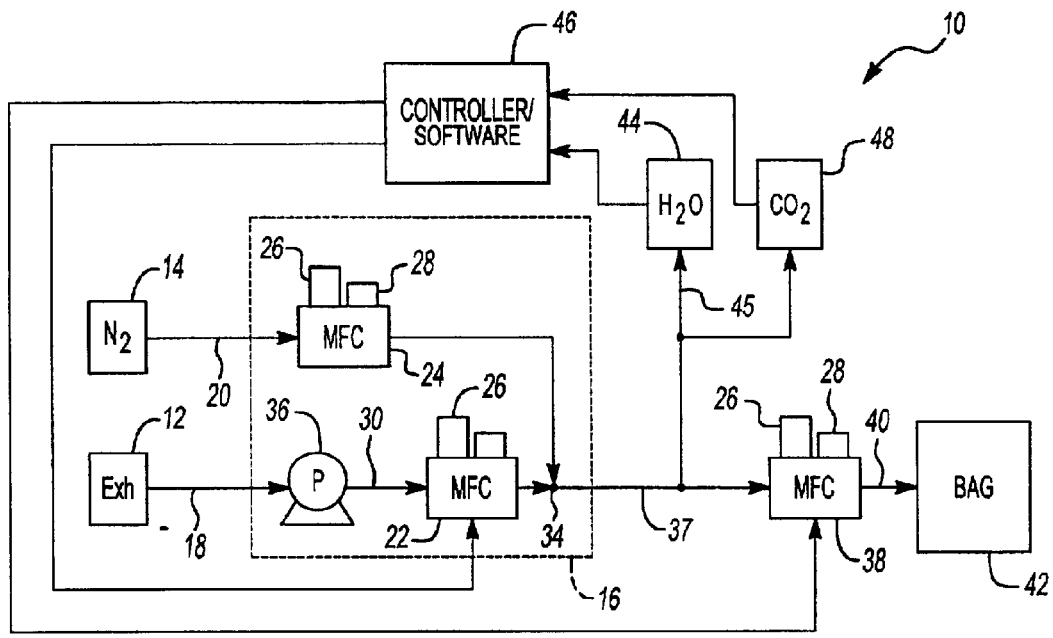
FIG. 1A is a schematic view of an exhaust emissions analysis system of the present invention.
Figure 1B:
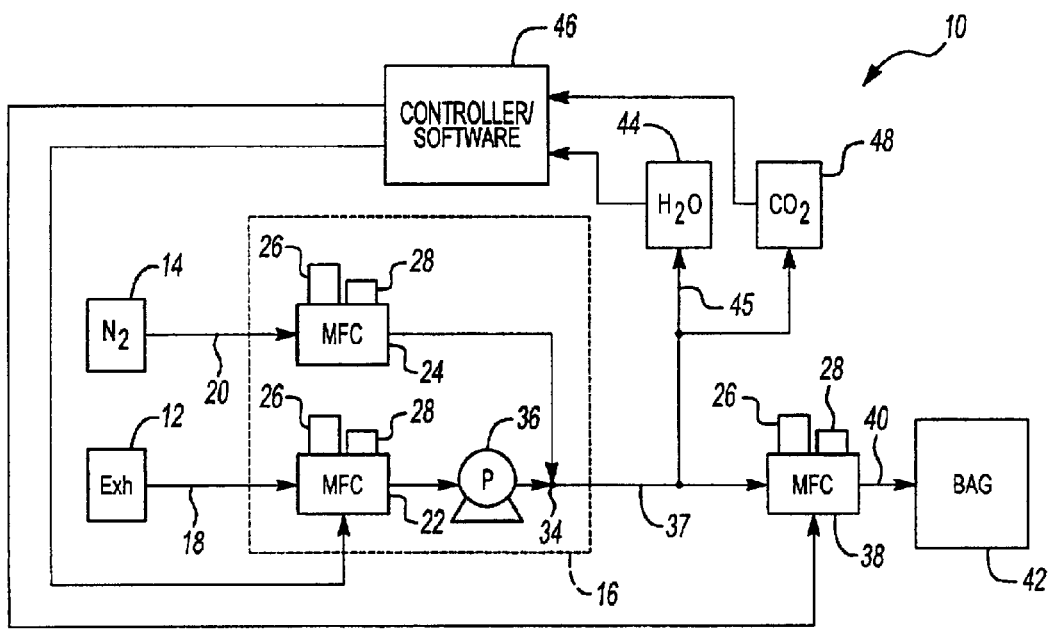
FIG. 1B is a schematic view of the system shown in FIG. 1A with the pump in another location.

An exhaust emissions analysis system 10 is shown in FIGS. 1A and 1B, which is highly schematic and depicts only a small portion of the exhaust emission test equipment. The system 10 includes an exhaust gas source 12, which is typically a probe inserted into a tailpipe of a vehicle for sampling the exhaust gases flowing through the tailpipe. The system 10 also includes a dilution gas source 14, which typically contains nitrogen, used to dilute the exhaust gas in a mini-diluter exhaust gas emission sampling system. The exhaust gas and dilution gas from the sources 12 and 14 enter a diluter unit 16 where the gases are mixed to a desired dilution ratio. It is highly desirable to maintain the desired dilution ratio throughout the vehicle emissions test to ensure sufficient accuracy and test integrity.

The exhaust gas 12 and dilution gas 14 sources are respectively connected to gas flow devices 22 and 24 by fluid conduits 18 and 20. With the present invention, the gas flow devices are preferably thermal mass flow controllers that include a flowmeter 26 and a valve 28, which may be obtained from Porter Instrument Company, Inc., series 200F mass flow controllers. As is known in the art, the meter 26 may include a mass flow sensor unit that includes a heater and two temperature sensors used to measure the specific heat of the gas flowing through the gas flow device to determine the flow rate. However, the gas flowing through the gas flow device must be known in order to obtain an accurate flow rate measurement, which we will discuss in more detail below. Thermal mass flow controllers also include amplification and linearization hardware and, in the case of a digital controller, software to ensure an accurate flow rate. The valve 28 typically is a solenoid valve, which may be opened and closed to adjust the gas flow and obtain the desired flow rate.

The gas flow devices 22 and 24 respectively include fluid conduits 30 and 32 that are joined at a connection 34 where the gases are mixed to provide an uncorrected dilution ratio. A pump 36 is required to transport the raw exhaust gas from the conduit 18 to the exhaust flow device 22, as shown in FIG. 1A. Alternatively, the pump 36 may be arranged to transport the raw exhaust gas from the exhaust flow device 22 to the connection 34, as shown in FIG. 1B. Another mass flow controller 38 follows the connection 34 through a fluid conduit 37. A fluid conduit 40 carries the diluted exhaust gas from the mass flow controller 38 to a sample bag 42 where the content of the exhaust gases are later analyzed to determine whether the vehicle's emissions are at an acceptable level. The mass flow controller 38 adjusts the flow of diluted exhaust gas to the bags 42 to correspond to the changing volume of exhaust gases expelled from the vehicle during the test.

The mass flow controllers 22 and 24 are set to a desired flow rate to obtain the desired dilution ratio. The mass flow controllers 22 and 24 are calibrated using a calibration gas, which is typically nitrogen or synthetic air. Since the measuring principle is based on the specific heat of the gas flowing through the mass flow controller, the accuracy of the flow rate is dependent upon the calibration gas used. Since nitrogen or synthetic air are also used as dilution gases, an accurate gas flow rate is obtained at the mass flow controller 24 upon calibration. However, since the specific heat of the exhaust gas generated during the vehicle emissions test is different than the specific heat of nitrogen, the flow rate of gas through the mass flow controller 22 is inaccurate during the vehicle emissions test unless corrected. This has been corrected in the prior art by sensing the water vapor in the diluted exhaust gas and adjusting the mass flow controller 38 to increase or decrease the flow of the sample gas into the bags 42. However, this still yields an inaccurate dilution ratio at the connection 34, which is undesirable in that it provides inaccurate test data and only masks the inaccuracy of the exhaust emission analysis system. Another common method has been to calibrate the exhaust gas mass flow controller 22 with a mixture of $CO_2$ and Nitrogen; this method does not account for changes of the exhaust gas composition and for the effects of the water content.

The present invention adjusts the mass flow controller 22 to obtain a correct dilution ratio at the connection 34. As can be appreciated by the equation below, the flow rate $Q_{read}$ may be adjusted to obtain the actual flow rate $Q_{actual}$ by multiplying by an adjustment factor.

$$Q_{actual} = Q_{read} \times \frac{K_{actual}}{K_{calibration\_gas}} = Q_{read} \times K_{actual},$$

for Nitrogen as calibration gas.

Since the K factor of the calibration gas is known, the actual K factor of the exhaust gas must be determined to adjust the flow rate at the mass flow controller 22. K-factors are provided by mass flow controller manufacturers to permit the user to adjust the flow rates of the mass flow controllers to provide an accurate flow rate. Several relevant K-factors are listed in the table below.

| Component | K-factor |
|---|---|
| $N_2$ | 1.000 |
| Air | 1.000 |
| $CO_2$ | 0.745 |
| $H_2O$ | 0.817 |

The water content of the exhaust gas is measured by a humidity sensor 44, shown in FIG. 1A, to determine the composition of the exhaust gas. The humidity sensor 44 is shown connected to the fluid conduit 37 by a fluid conduit 45 after the pump 36 to measure the diluted exhaust gases. However, it is to be understood that the water content of the exhaust gas may be measured elsewhere. Preferably, the carbon dioxide in the exhaust gas is also determined to further increase the accuracy of determining the K-factor for the exhaust emissions. Combustion stoichiometry is used to determine the composition of the combustible mixture and the composition of the products of reaction to calculate the K-factor for each product of reaction. Because the concentration of carbon dioxide and water content is measured in the dilute exhaust gas, the concentration of raw exhaust gas values have to be calculated and applied to the calculation of the K-factor, which may be represented by the equation below.

$$K_{actual} = \frac{1}{\left(\frac{c_{H_2O} \cdot q}{K_{H_2O}} + \frac{c_{CO_2} \cdot q}{K_{CO_2}} + \frac{1 - c_{H_2O} \cdot q - c_{CO_2} \cdot q}{K_{N_2}}\right)}$$

For the equation above, $c_{H2O}$ is the portion of exhaust gases that represents water. Similarly, $c_{CO2}$ is the portion of the exhaust gases that represents carbon dioxide. The present dilution ratio q is the ratio between the total flow rate of both mass flow controllers 22 and 24 to the flow rate of the raw exhaust mass flow controller 22, which must be applied because the humidity and carbon dioxide is determined downstream after dilution of the sample. Since the K-factors for water and carbon dioxide are known through the information provide by the mass flow controller manufacturer, the K-factor of the remaining components of the exhaust gas is the only unknown, which is roughly equal to the K-factor for nitrogen. As a result, $K_{actual}$ may be calculated and provides an adjustment factor for the flow rate through the mass flow controller 22. The carbon dioxide concentration can be directly measured with an analyzer, shown at 48 in FIG. 1A, or calculated out of the combustion air and fuel flow and the fuel composition, as schematically shown at 48 in FIG. 1B. In this manner, the carbon dioxide analyzer 48 may be omitted and its function may be performed by the controller 46. The water content value will be measured as relative humidity in the diluted exhaust gas and is preferably converted to a volume fraction. For this calculation, the pressure and temperature needs to be taken. Information from the water 44 and carbon dioxide 48 analyzers are sent to a controller 46 for calculation of the K-factor. The K-factor is then translated into a command signal which is sent to the mass flow controller 22 to adjust the flow rate of a controller based upon the exhaust gas flowing through it to obtain a corrected dilution ratio at the connection 34.

In addition to correcting the mass flow controller 22, the dilute exhaust mass flow controller 38 may also be corrected so that an accurate volume is sampled into the bags 42. To this end, a command signal is sent from the controller 46 to the mass flow controller 38 to correct the flow rate. The formula shown below is used to calculate the K-factor out of the concentrations in the dilute exhaust gas, and therefore, q does not have to be used in the calculation.

$$K_{actual} = \frac{1}{\left(\frac{c_{H_2O}}{K_{H_2O}} + \frac{c_{CO_2}}{K_{CO_2}} + \frac{1 - c_{H_2O} - c_{CO_2}}{K_{N_2}}\right)}$$

Figure 2:
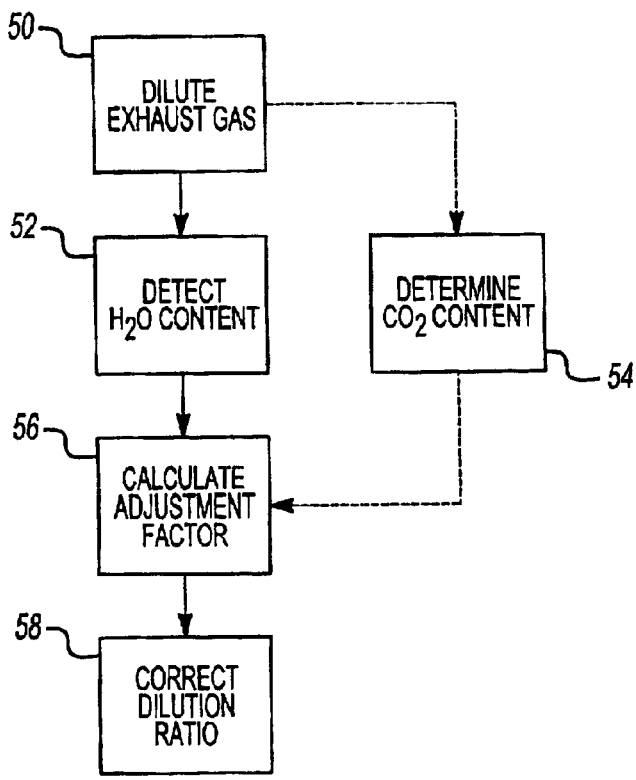
FIG. 2 is a flowchart depicting the method of using the present invention analysis system.

In operation, the exhaust gas is diluted, as indicated at block 50 in FIG. 2. The water content is detected as indicated at block 52, and preferably the carbon dioxide is also determined as indicated at block 54. The adjustment or K-factor is calculated by the controller 46 in the manner discussed above, as indicated at block 56. The K-factor adjusts for the difference in specific heat between the calibration gas, which is nitrogen or synthetic air, and the exhaust gas flowing through the mass flow controller 22. The K-factor is continually calculated to adjust for the content of the exhaust gas flowing through the mass flow controller 22 at any given moment. This ensures that the correct dilution ratio is obtained throughout the vehicle emissions test. The K-factor is sent in the form of a signal to the mass flow controller 22 to obtain the correct dilution ratio as indicated at block 58.

Figure 3:
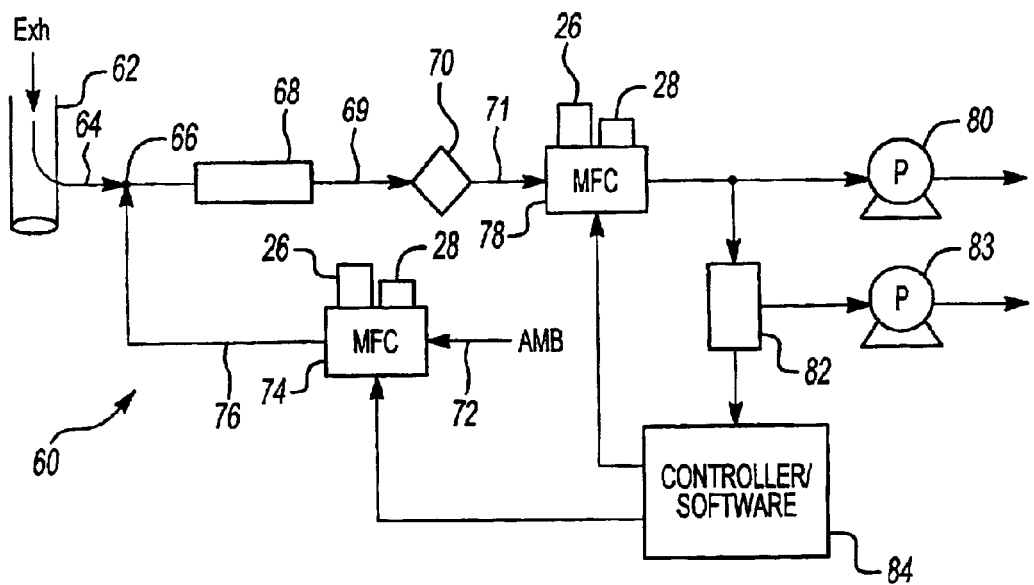
FIG. 3 is a schematic view of a present invention particulate sampler.

The present invention may be applied to a particular sampler in a manner similar to that described above relative to mini-diluters. Referring to FIG. 3, a particulate sampler 60 is shown. The particulate sampler 60 includes a probe 64 inserted into an exhaust pipe 62 for collecting a portion of the exhaust gases expelled from the vehicle. The sampler 60 also includes a mixer 66 that receives air from a conduit 72 and mixes the air with the exhaust gas. The diluted exhaust gas flows through a tunnel 68 and through a conduit 69 to a filter 70 where particulates from the diluted exhaust gas is collected for subsequent analysis.

The control of air received from conduit 72 to conduit 76 is controlled by a mass flow controller 74 having a controller 26 and valve 28 similar to those discussed above. Flow of diluted exhaust gas from the filter 70 is controlled by mass flow controller 78, which includes controller 26 and valve 28. The diluted exhaust gas is pulled from the conduit 71 through the mass flow controller 78 by a pump 80.

The water content and/or carbon dioxide content may be determined at device or devices 82 by a direct measurement or by calculation, such as by calculating the carbon dioxide content. A portion of the diluted exhaust used for this determination is pulled through the device 82 by pump 83. The data from the device 82 is analyzed by the control device 84 and an adjustment factor is calculated in a manner similar to that discussed above relative to the mini-diluter. The control device 84 sends a flow rate command signal to one or both of the mass flow controllers 74 and 78 corresponding to the adjustment factor to adjust the gas flow rate there through to provide a corrected dilution ratio at the mixer 66.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

What is claimed is:

1. An exhaust emissions analysis system comprising:
   an exhaust and dilution gas source respectively providing exhaust and dilution gases;
   a diluter unit including exhaust and dilution gas flow devices fluidly connected to said exhaust and dilution gas sources respectively, said flow devices defining a gas flow rate of gas from its respective gas source with said gas flow devices fluidly connected at a connection providing a diluted exhaust gas having an uncorrected dilution ratio;
   a humidity measurement device measuring water content of one of exhaust and said diluted exhaust gases and producing a water content signal corresponding to said water content; and
   a control device receiving said water content signal and calculating an adjustment factor relating to said water content, said control device sending a flow rate command signal corresponding to said adjustment factor to one of said exhaust and dilution gas flow devices to adjust said gas flow rate of said one of said exhaust and dilution gas flow devices to provide a corrected dilution ratio at said connection.

2. The system according to claim 1, further including a carbon dioxide device determining carbon dioxide content in said one of said exhaust and diluted exhaust gases and producing a carbon dioxide content signal corresponding to said carbon dioxide content, said control device receiving said carbon dioxide content signal and calculating said adjustment factor relating to said water and said carbon dioxide contents.

3. The system according to claim 2, wherein said carbon dioxide device is a carbon dioxide measurement device measuxing said carbon dioxide content in said one of said exhaust and diluted exhaust gases.

4. The system according to claim 2, wherein said carbon dioxide device is a portion of said control device calculating said carbon dioxide content in sand one of said exhaust and diluted exhaust gases.

5. The system according to claim 2, wherein said carbon dioxide device determines said carbon dioxide content in said diluted exhaust gas.

6. The system according to claim 1, wherein said control device includes hardware and software.

7. The system according to claim 1, wherein said humidity measurement device measures said water content of said diluted exhaust gas.

8. The system according to claim 1, wherein said control device sends said flow rate command signal to said dilution gas flow device.

9. The system according to claim 8, wherein said exhaust gas flow device is a first mass flow controller.

10. The system according to claim 9, wherein said dilution gaas flow device is a second mass flow controller.

11. The system according to claim 1, further including a pump carrying said exhaust gas from said connection to a diluted sample gas flow device fluidly connected to a diluted sample gas bag.

12. The system according to claim 11, wherein diluted sample gas flow device is a third mass flow controller.

13. The system according to claim 11, wherein said humidity measurement device measures said water content of said diluted exhaust gas between said pump and said diluted sample gas flow device.

14. The system according to claim 1, wherein said adjustment factor is a K-factor that relates to a specific heat of said exhaust gas relative to a calibration gas specific heat.

15. A method of correcting measurement of exhaust emissions comprising the steps of:
   a) diluting an exhaust gas with a dilution gas to an uncorrected dilution ratio;
   b) detecting water content in the exhaust gases;
   c) calculating an adjustment factor based upon the water content; and
   d) applying the adjustment factor to modify the flow of one of the exhaust and dilution gases to a corrected dilution ratio.

16. The method according to claim 15, whrein step a) includes selecting a dilution gas flow rate set point and an exhaust gas flow rate set point to obtain the uncorrected dilution ratio.

17. The method according to claim 15, further including the steps of determining carbon dioxide content in the exhaust gas, and calculating the adjustment factor based upon the water content and the carbon dioxide content.

18. The method according to claim 17, wherein the step of determining the carbon dioxide content includes detecting the carbon dioxide content.

19. The method according to claim 17, wherein the step of determining the carbon dioxide content includes calculating the carbon dioxide content.

20. The method according to claim 15, wherein step d) includes calculating the adjustment factor to obtain a K-factor that relates to a specific heat of the exhaust gas relative to a calibration gas specific heat.

21. The method according to claim 15, wherein step b) includes detecting the water content in diluted exhaust gases.

22. The method according to claim 15, wherein step d) includes modifying the flow by controlling a valve in a mass flow controller.

23. The method according to claim 15, further including providing a particulate sampler supplying the exhaust gas.

24. The method according to claim 23, wherein the dilution gas is air.

25. An exhaust emissions analysis system comprising:
   an exhaust and dilution gas source respectively providing exhaust and dilution gases;
   a diluter unit including exhaust and dilution gas flow devices fluidly connected to said exhaust and dilution gas sources respectively, said flow devices defining a gas flow rate of gas from its respective gas source with said gas flow devices fluidly connected at a connection providing a diluted exhaust gas having an uncorrected dilution ratio;
   a carbon dioxide device determining carbon dioxide content of one of exhaust and said diluted exhaust gases and producing a carbon dioxide content signal corresponding to said carbon dioxide content; and
   a control device receiving said carbon dioxide content signal and calculating an adjustment factor relating to said carbon dioxide content, said control device sending a flow rate command signal corresponding to said adjustment factor to one of said exhaust and dilution gas flow devices to adjust said gas flow rate of said one of said exhaust and dilution gas flow devices to provide a corrected dilution ratio at said connection.

26. The system according to claim 25, further including a humidity measurement device measuring water content in said one of said exhaust and diluted exhaust gases and producing a water content signal corresponding to said water content, said control device receiving said water content signal and calculating said adjustment factor relating to said water and said carbon dioxide contents.

27. The system according to claim 25, wherein said carbon dioxide device is a carbon dioxide measurement device measuring said carbon dioxide content in said one of said exhaust and diluted exhaust gases.

28. The system according to claim 25, wherein said carbon dioxide device is a portion of said control device calculating said carbon dioxide content in said one of said exhaust and diluted exhaust gases.

29. The system according to claim 25, wherein said carbon dioxide device determines said carbon dioxide content in said diluted exhaust gas.

30. The system according to claim 25, wherein said control device includes hardware and software.

31. The system according to claim 26, wherein said humidity measurement device measures said water content of said diluted exhaust gas.

32. The system according to claim 25, wherein said control device sends said flow rate command signal to said dilution gas flow device.

33. The system according to claim 32, wherein said exhaust gas flow device is a first mass flow controller.

34. The system according to claim 33, wherein said dilution gas flow device is a second mass flow controller.

35. The system according to claim 25, further including a pump carrying said exhaust gas from said connection to a diluted sample gas flow device fluidly connected to a diluted sample gas bag.

36. The system according to claim 35, wherein diluted sample gas flow device is a third mass flow controller.

37. The system according to claim 35, wherein said humidity measurement device measures said water content of said diluted exhaust gas between said pump and said diluted sample gas flow device.

38. The system according to claim 25, wherein said adjustment factor is a K-factor that relates to a specific heat of said exhaust gas relative to a calibration gas specific heat.

39. A method of correcting measurement of exhaust emissions comprising the steps of:
   a) diluting an exhaust gas with a dilution gas to an uncorrected dilution ratio;
   b) determining carbon dioxide content in the exhaust gases;
   c) calculating an adjustment factor based upon the carbon dioxide content; and
   d) applying the adjustment factor to modify the flow of one of the exhaust and dilution gases to a corrected dilution ratio.

40. The method according to claim 39, wherein step a) includes selecting a dilution gas flow rate set point and an exhaust gas flow rate set point to obtain the uncorrected dilution ratio.

41. The method according to claim 39, further including the steps of measuring water content in the exhaust gas, and calculating the adjustment factor based upon the water content and the carbon dioxide content.

42. The method according to claim 39, wherein the step of determining the carbon dioxide content includes measuring the carbon dioxide content.

43. The method according to claim 39, wherein the step of determining the carbon dioxide content includes calculating the carbon dioxide content.

44. The method according to claim 39, wherein step d) includes calculating the adjustment factor to obtain a K-factor that relates to a specific heat of the exhaust gas relative to a calibration gas specific heat.

45. The method according to claim 41, wherein step b) includes detecting the water content in diluted exhaust gases.

46. The method according to claim 39 wherein step d) includes modifying the flow by controlling a valve in a mass flow controller.

47. The method according to claim 39, further including providing a particulate sampler supplying the exhaust gas.

48. The method according to claim 39, wherein the dilution gas is air.

49. An exhaust emissions analysis system comprising:
a dilution source providing dilution gas;
a particulate sampler having a probe providing exhaust gas and a mixer introducing said dilution gas to said exhaust gas to provide a diluted exhaust gas having an uncorrected dilution ratio; diluted exhaust and dilution gas flow devices fluidly connected to said diluted exhaust and dilution gas sources respectively, said flow devices defining a gas flow rate of gas from its respective gas source;
a humidity measurement device measuring water content of one of exhaust and said diluted exhaust gases and producing a water content signal corresponding to said water content; and
a control device receiving said water content signal and calculating an adjustment factor relating to said water content, said control device sending a flow rate command signal corresponding to said adjustment factor to one of said diluted exhaust and dilution gas flow devices to adjust said gas flow rate of said one of said diluted exhaust and dilution gas flow devices to provide a corrected dilution ratio at said mixer.

50. The system according to claim 49, wherein a filter is arranged between said particulate sampler and said diluted exhaust gas flow device.

51. The system according to claim 49, wherein said dilution gas is air.

52. The system according to claim 49, further including a carbon dioxide device determining carbon dioxide content in said one of said exhaust and diluted exhaust gases and producing a carbon dioxide content signal corresponding to said carbon dioxide content, said control device receiving said carbon dioxide content signal and calculating said adjustment factor relating to said water and said carbon dioxide contents.

53. The system according to claim 52, wherein said carbon dioxide device is a carbon dioxide measurement device measuring said carbon dioxide content in said one of said exhaust and diluted exhaust gases.

54. The system according to claim 52, wherein said carbon dioxide device is a portion of said control device calculating said carbon dioxide content in said one of said exhaust and diluted exhaust gases.

55. The system according to claim 52, wherein said carbon dioxide device determine said carbon dioxide content in said diluted exhaust gas.

56. The system according to claim 49, wherein said control device includes hardware and software.

57. The system according to claim 49, wherein said humidity measurement device measures said water content of said diluted exhaust gas.

58. The system according to claim 49, wherein said control device send said flow rate command signal to said dilution gas flow device.

59. The system according to claim 58, wherein said dilution gas flow device is a first mass flow controller.

60. The system according to claim 59, wherein said exhaust gas flow device is a second mass flow controller.

61. An exhaust emissions analysis system comprising:
a dilution source providing dilution gas;
a particulate sampler having a probe providing exhaust gas and a mixer introducing said dilution gas to said exhaust gas to provide a diluted exhaust gas having an uncorrected dilution ratio; diluted exhaust and dilution gas flow devices fluidly connected to said diluted exhaust and dilution gas sources respectively, said flow devices defining a gas flow rate of gas from its respective gas source;
a carbon dioxide device determining content of one of exhaust and said diluted exhaust gases and producing a carbon dioxide content signal corresponding to said carbon dioxide content; and
a control device receiving said carbon dioxide content signal and calculating an adjustment factor relating to said carbon dioxide content, said control device sending a flow rate command signal corresponding to said adjustment factor to one of said diluted exhaust and dilution gas flow devices to adjust said gas flow rate of said one of said diluted exhaust and dilution gas flow devices to provide a corrected dilution ratio at said mixer.

62. The system according to claim 61, wherein a filter is arranged between said particulate sampler and said diluted exhaust gas flow device.

63. The system according to claim 61, wherein said dilution gas is air.

64. The system according to claim 61, further including a humidity measurement device measuring water content in said one of said exhaust and diluted exhaust gases and producing a water content signal corresponding to said water content, said control device receiving said water content signal and calculating said adjustment factor relating to said water and said carbon dioxide contents.

65. The system according to claim 64, wherein said carbon dioxide device is a carbon dioxide measurement device measuring said carbon dioxide content in said one of said exhaust and diluted exhaust gases.

66. The system according to claim 64, wherein said carbon dioxide device is a portion of said control device calculating said carbon dioxide content in said one of said exhaust and diluted exhaust gases.

67. The system according to claim 64, wherein said water measurement device measures said water content in said diluted exhaust gas.

68. The system according to claim 61, wherein said control device includes hardware and software.

69. The system according to claim 61, wherein said carbon dioxide device determines said carbon dioxide content of said diluted exhaust gas.

70. The system according to claim 61, wherein said control device send said flow rate command signal to said dilution gas flow device.

71. The system according to claim 70, wherein said dilution gas flow device is a first mass flow controller.

72. The system according to claim 71, wherein said exhaust gas flow device is a second mass flow controller.

* * * * *

UNITED STATES PATENT AND TRADEMARK OFFICE
CERTIFICATE OF CORRECTION

PATENT NO. : 6,823,268 B2
DATED : November 23, 2004
INVENTOR(S) : Silvis et al.

It is certified that error appears in the above-identified patent and that said Letters Patent is hereby corrected as shown below:

Title page,
Item [75], Inventors, "Geraki Marek" should be -- Gerald Marek --.

Column 6,
Line 43, "measuxing" should be -- measuring --.
Line 47, "sand" should be -- said --.
Line 63, "gaas" should be -- gas --.

Column 7,
Line 21, "whrein" should be -- wherein --.

Signed and Sealed this

Fifteenth Day of February, 2005

JON W. DUDAS
*Director of the United States Patent and Trademark Office*